United States Patent [19]

Platsch

[11] Patent Number: 5,090,626
[45] Date of Patent: Feb. 25, 1992

[54] APPARATUS FOR PRODUCING A VERY THIN MIST OF POWER AND CONTROLS FOR PRODUCING THIN MIST OF POWER

[75] Inventor: Hans G. Platsch, Stuttgart, Fed. Rep. of Germany

[73] Assignee: Industrieelektronik Dr-Ing Walter Klaschika GmbH & Co., Fed. Rep. of Germany

[21] Appl. No.: 623,962
[22] PCT Filed: May 24, 1989
[86] PCT No.: PCT/EP89/00571
§ 371 Date: Nov. 27, 1990
§ 102(e) Date: Nov. 27, 1990
[87] PCT Pub. No.: WO89/11917
PCT Pub. Date: Dec. 14, 1989

[30] Foreign Application Priority Data

Jun. 6, 1988 [DE] Fed. Rep. of Germany ....... 3819203

[51] Int. Cl.$^5$ .............................................. B67D 5/08
[52] U.S. Cl. ...................................... 239/654; 239/71
[58] Field of Search .................. 239/71, 74, 654, 655, 239/345, 346; 222/56, 235, 630, 637; 366/151, 154, 132; 355/246, 247

[56] References Cited

U.S. PATENT DOCUMENTS

| 2,301,136 | 11/1942 | Moreland et al. | 222/56 |
| 3,091,368 | 5/1963 | Harley et al. | 222/56 |
| 3,731,743 | 5/1973 | Marshall | 239/71 |
| 4,503,806 | 3/1985 | Prusak et al. | 239/74 |
| 4,702,931 | 10/1987 | Falcoff | 239/71 |
| 4,815,414 | 3/1989 | Duffy et al. | 239/655 |

FOREIGN PATENT DOCUMENTS

| 222258 | 5/1987 | European Pat. Off. | 239/74 |
| 151834 | 11/1979 | Japan | 222/56 |
| 277720 | 11/1989 | Japan | 222/56 |

Primary Examiner—Andres Kashnikow
Assistant Examiner—Lesley D. Morris
Attorney, Agent, or Firm—Fred Philpitt

[57] ABSTRACT

An apparatus for generating a very thin mist of powder with a device for measuring the flow of powder from a supply container and controlling the flow of the powder to an atomization chamber, which includes a device for periodically diverting the flow of the powder past the measuring device so as to determine the effects of aging and impurities on the measuring device and to compensate the measuring device for such effects.

18 Claims, 4 Drawing Sheets

APPARATUS FOR PRODUCING A VERY THIN MIST OF POWER AND CONTROLS FOR PRODUCING THIN MIST OF POWER

The invention relates to a dusting apparatus.

Dusting apparatus of this type, such as are described for example in DE-A-26 37 875, are used in printing machines, in order to provide freshly printed sheets or endless webs with a thin covering of dust, which prevents the sheets from sticking together. If the dusting apparatus dispenses too little powder, then this object is not reliably achieved, if too much powder is applied to the printed products, then this results in an unpleasant feel of the product for the user and increases the costs for dusting. Sometimes, an excessive layer of powder is also a drawback at the time of subsequent mechanical treatment of the printed products, since reproducible friction ratios do not exist. In a dusting apparatus according to DE-A-26 37 875, the powder requirement is ascertained relatively roughly by a sensor, which produces a signal proportional to the operating speed of the printing machine.

Hitherto the actual monitoring of the thickness of the powder covering applied by the dusting apparatus to the printed products took place due to the fact that a black control sheet was allowed to travel through the dusting apparatus and the whitening on the sheet was monitored optically. However, this type of control is obviously not possible during routine operation, so that in this case careful supervision by the operator was necessary in order to ascertain both a shortage as well as an excess of powder, which resulted from variations in the powder properties (for example increase in the moisture content) and the adjustment of the dusting apparatus in long term use.

My dusting apparatus described hereafter should therefore be developed by the present invention so that a uniform quality of the powder coating applied to the printed products is guaranteed even during production. This object is achieved according to the invention by a dusting apparatus according to claim 1. In the dusting apparatus according to the invention, the density of a powder stream falling freely from the dosing device into the atomization device is measured. This density is as a whole still relatively high, so that when using less sensitive measuring devices, a great variation of the measurement signal is obtained. If one were to measure variations of density directly in the mist produced, which is obtained by atomization of the powder in a carrier gas, one would have to use very sensitive measuring devices, which in addition still react very sensitively to interference effects.

Since, in the dusting apparatus according to the invention, a relative movement between the free-falling powder stream and the measurement gate is carried out at regular intervals, one can use the output signal of the measurement gate at those times when the powder stream does not pass therethrough, for the purpose of compensating for interference effects caused by impurities or ageing. Thus, in particular, it is not necessary to incorporate a cleaning device in the dusting apparatus, which cleaning device keeps the measuring section free of impurities continuously or intermittently. Also, temperature influences are obviated in this way.

Apparatus are known per se for determining the suspended particle concentration in gases, in which the optical parts of the measurement gate are placed at regular intervals in a reference path, which is free from suspended particles. Examples of this are EP-A-00 47 049 and CH-A-567 721.

In these known measuring apparatus for determining the suspended particle content, either a closed light path or a tube through which a pure gas passes, is placed by an electric motor at regular intervals in the measuring gate or the measuring gate is shifted accordingly. In this case, precise evaluation electronics are required on account of the generally only low fluctuations of the optical density. On the other hand, according to the invention, the density of the powder stream falling freely into the atomization device from the dosing device is measured.

Advantageous developments of the invention are described in the Sub-claims.

If one produces the relative movement between the measurement gate and powder stream according to claim 2, then this takes place with very simple, mechanical means, which are not susceptible to disturbances. A flexible hose also disturbs the flow of the powder stream only little, since smooth transition points are present throughout in the direction of flow.

The development of the invention according to another embodiment is an advantage with regard to a reliable and simple deflection of the free end of the piece of hose guiding the powder stream, controlled by a programme control.

The development of the invention according to another embodiment prevents powder from accumulating on shoulders or projections of the apparatus housing, in the vicinity of the measuring section.

With the development of the invention according to another embodiment it is ensured that the flow of the powder stream over the deflection surface leading back to the axis of the apparatus takes place in a particularly careful and uniform manner, which is once more an advantage with regard to avoiding accumulations of powder and the formation of a vortex before the powder stream enters the atomization device. A uniform, laminar entry of the powder stream into the atomization device is however an advantage once again with regard to a homogeneous, uniform mist formation.

In a dusting apparatus according to another embodiment, one always has exactly the same conditions for the flow of the powder stream, irrespective of whether the powder stream is just passing through the measuring gate or has just been removed from the latter for re-calibration of the measuring device.

The development of the invention according to another embodiment allows, in a simple manner, the strictly synchronous movement of the transmitter and receiver of the measurement gate, without impeding the powder stream.

With the development of the invention according to another embodiment, a particularly uniform production of mist is guaranteed.

Also, the development of the invention according to another embodiment is an advantage with regard to a uniform mist formation and with regard to a uniform sucking-in of the powder stream into the atomization device.

According to another embodiment, one can optimize the flow conditions in the atomization device, upstream and downstream thereof according to the respective specific properties of the powder used and according to the respectively desired flow speed of the mist.

The development of the invention according to another embodiment allows a uniform distribution of the mist produced at a plurality of discharge nozzles, which are arranged distributed transversely above the printed product.

With the developments of the invention according to another embodiment, it is ensured that the sensitivity of the measuring device as a whole is kept substantially constant. Thus, the accuracy of adhering to the desired mist composition is maintained even over very long periods of time.

The invention will be described in detail hereafter by means of embodiments, referring to the drawings, in which.

Figure 1:
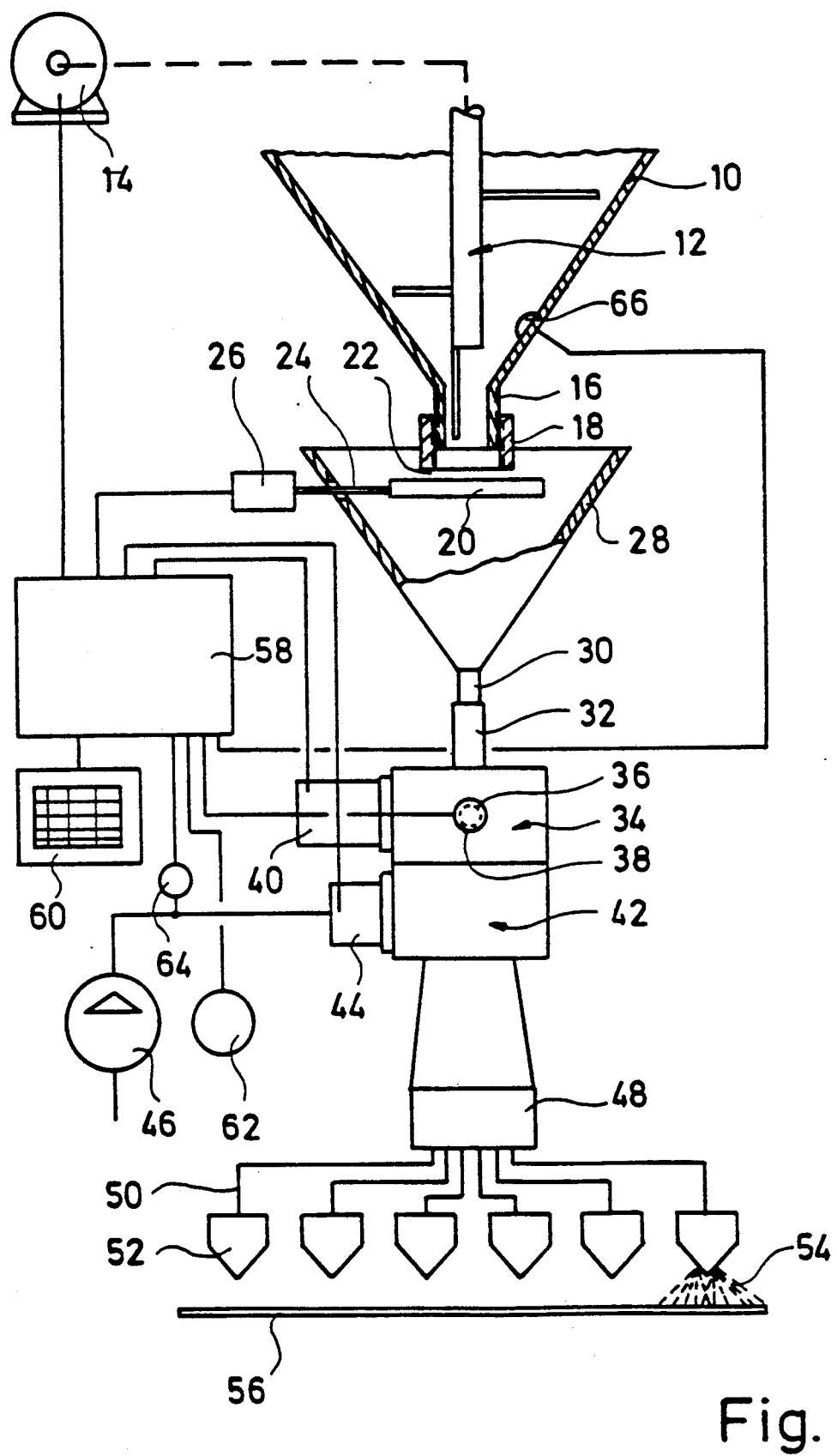
FIG. 1 is a diagrammatic side view of a dusting apparatus for use in a printing machine, shown in partial axial section.
Figure 2:
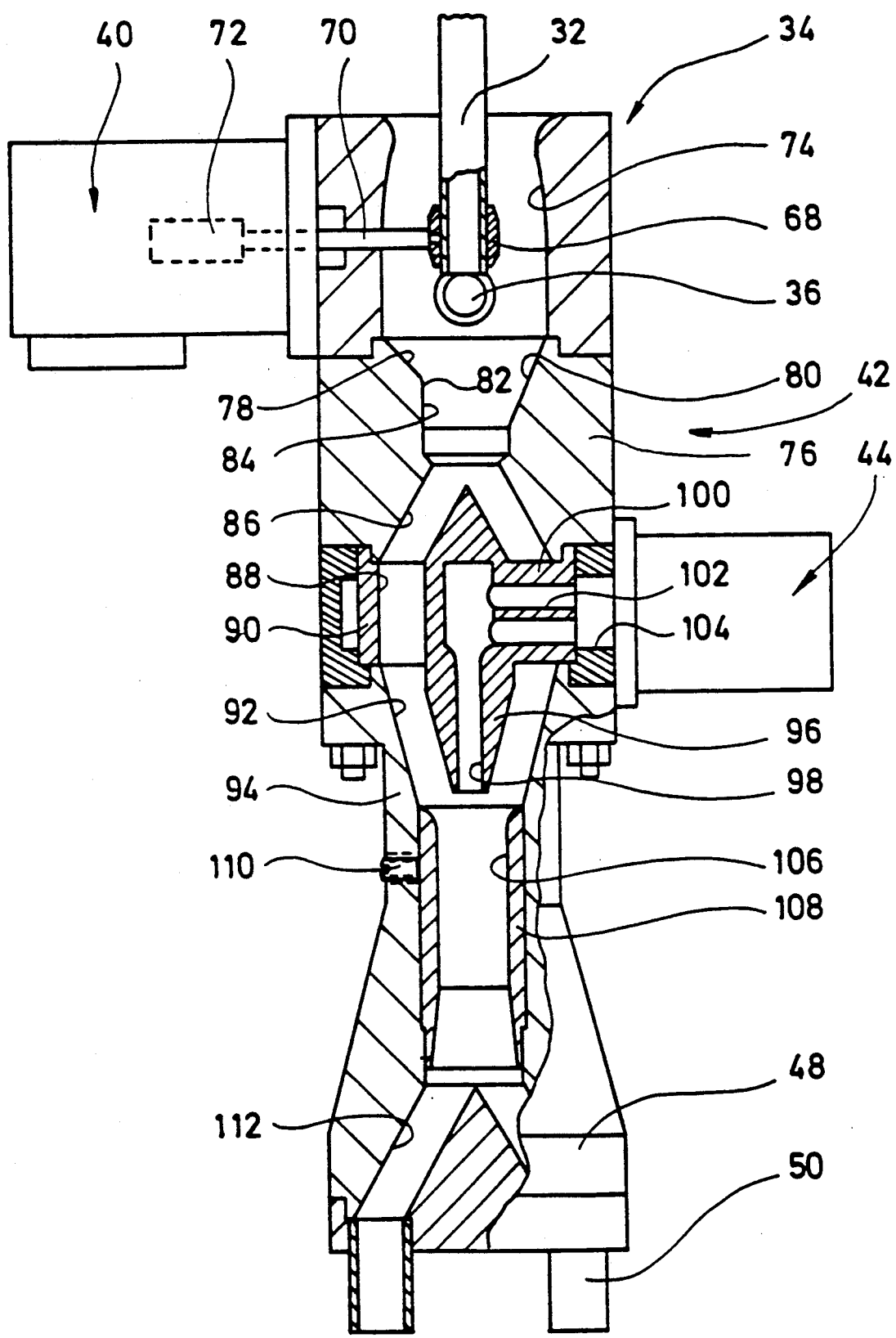
FIG. 2 is an axial section through a practical embodiment of a lower unit of the dusting apparatus shown in FIG. 1, in which the powder is atomized, the density of the powder stream to be atomized is measured and the mist produced is distributed uniformly to various working lines.
Figure 3:
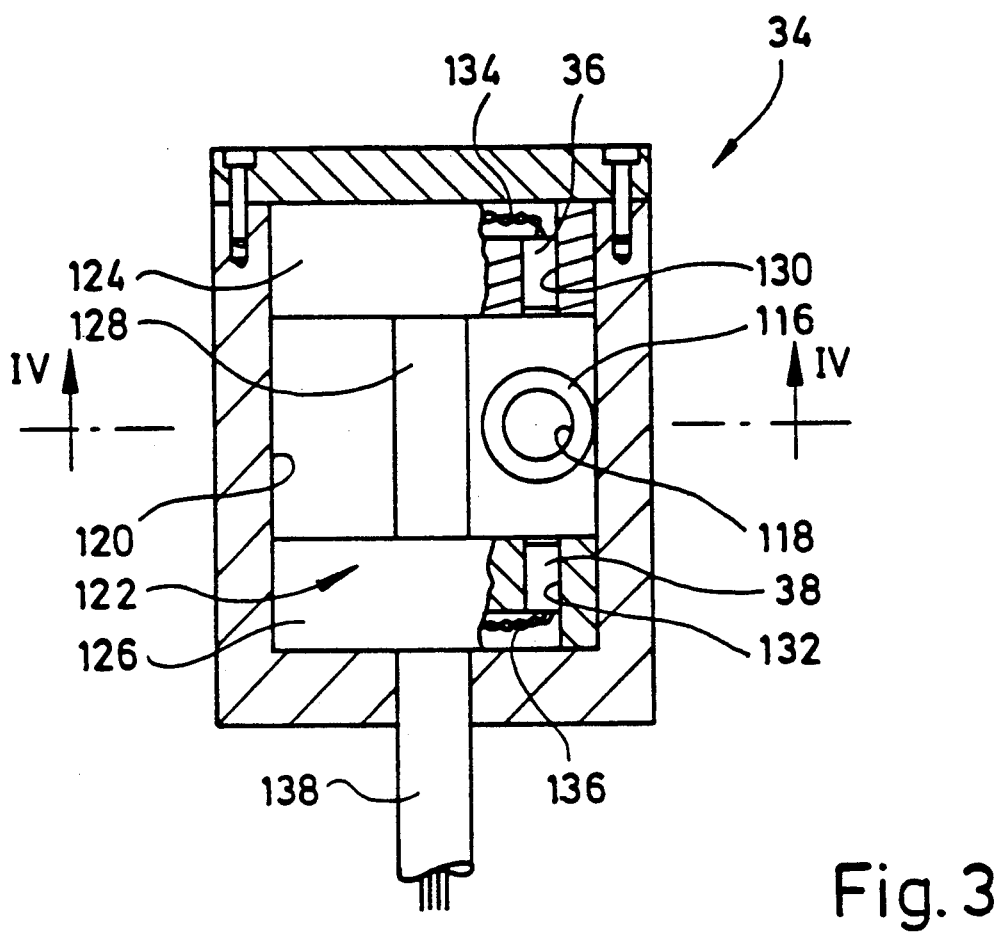
FIG. 3 is a horizontal section through a modified measuring device for determining the powder stream supplied to the atomization device.
Figure 4:
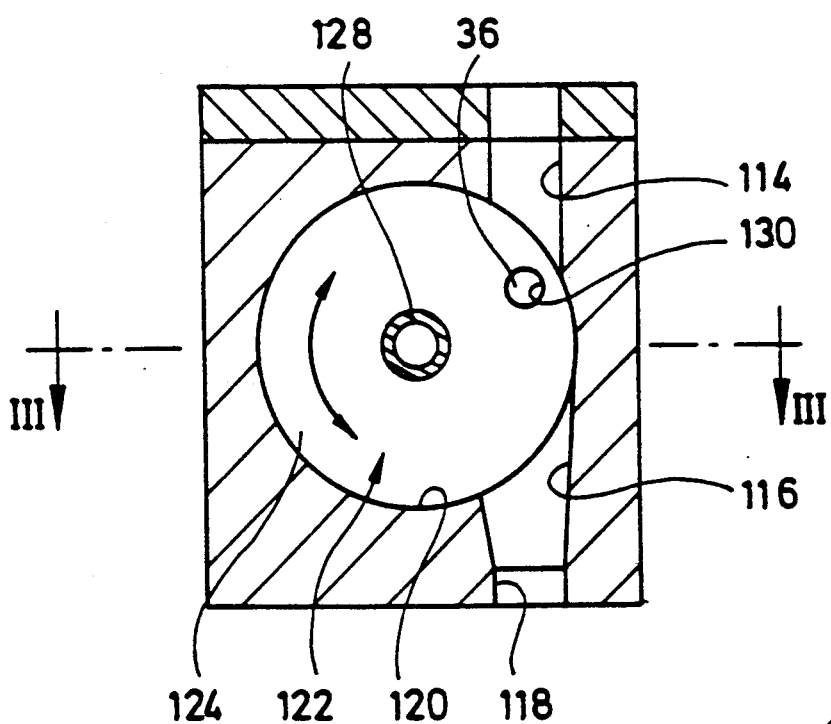
FIG. 4 is a vertical section through the measuring device according to FIG. 3, on section line IV—IV.

In FIG. 1, the reference numeral 10 designates a storage container, which is filled with a powder material to be applied to printed products in the form of a thin dust coating, which is not shown in FIG. 1. Current powder materials of this type, which prevent freshly printed products from sticking together, are for example maize starch, $CaCO_3$ and sugar with particle sizes of 10 to $50\mu$, usually between 15 and $20\mu$.

The powder material is kept in the fluid state in the storage container 10 by a stirrer designated generally by the reference numeral 12. The stirrer 12 is driven by an electric motor 14.

A metering sleeve 18 is screwed to a discharge nozzle 16 located at the lower end of the storage container 10. This dosing sleeve 18 together with a horizontal dosing plate 20 located therebelow defines a dosing gap 22, whereof the axial dimension can be adjusted by rotating the dosing sleeve 18.

The dosing plate 20 is connected by way of a rod 24 to an oscillating drive 26 and is moved to and fro in the horizontal direction by the latter at a typical frequency of 250 Hz, the amplitude of this movement being adjustable. The coarse adjustment of the powder stream removed from the storage container 10, determined by way of the size of the dosing gap 22, can be finely adjusted by way of the amplitude of the movement of the dosing plate 20.

The powder stream trickling down over the edges of the dosing plate 20 is caught by a hopper 28, which comprises a delivery nozzle 30 at the lower end. Fitted to the latter is the upper end of a flexible hose 32, which leads into a measuring chamber designated generally by the reference numeral 34. The powder stream obtained by way of the hose 32 falls freely downwards in the latter, in which case it falls through a measuring gate, which is formed by a light source 36, for example a light-emitting diode, as well as a light detector 38, for example a photodiode.

The free lower end of the hose 32 may be deflected within the measuring chamber 34 laterally with respect to the connecting line between the light source 36 and light detector 38, as will be described in more detail hereafter with reference to FIG. 2 and for producing this movement a solenoid 40 is fitted to the measuring chamber 34.

The powder stream emerging downwards from the measuring chamber 34 passes into an atomization chamber designated generally by the reference numeral 42, to which a compressed air stream is supplied by way of a solenoid valve 44. Features of the atomization chamber 42 will likewise be described in more detail hereafter.

The solenoid valve 44 is connected to the output of a compressor 46.

Located below the atomization chamber 42 is a distributor housing 48, in which the thin mist produced from the compressed air and powder stream is distributed to a plurality of working lines 50, which lead to nozzle bars 52 extending at right angles to the plane of the drawing of FIG. 1. The latter apply mist jets 54 substantially homogeneously to the upper side of a fresh printed product.

A digital programme control designated generally by the reference numeral 58 energizes the electro motor 14, the oscillating drive 26, the solenoid 40 and the solenoid valve 44. Basic parameters for the respective operation may be fed into the latter by way of an input panel 60, in particular the length and width of the sheets to be dusted, the desired density of the mist directed towards the upper side of the printed product, basic properties of the powder material to be atomized, speed of movement of the printed product etc.

The programme control 58 furthermore cooperates with a sheet detector 62, which responds when the front edge of the printed product reaches the nozzle bars 52 and is de-energized when the rear edge of the printed product has left the nozzle bars 52. The programme control 58 is also connected to the output of a pressure sensor 64, which monitors the delivery pressure of the compressor 46. The programme control 58 also receives the output signal of a level sensor 66, which is located at the lower end of the storage container 10 and responds when sufficient powder material is no longer available for further operation of the dusting apparatus.

For regulating a constant powder stream in the atomization chamber, the programme control 58 is connected to the output of the light detector 38 and adjusts the oscillating amplitude and/or oscillating frequency of the dosing plate 20 so that the same optical density, thus also the same material density of the powder stream is always maintained in the measuring section formed by the light source 36 and the light detector 38.

As can be seen from FIG. 2, the free lower end of the hose 32 is fixed radially in a ring 68, which is in turn connected by way of a plunger 70 to the armature 72 of the solenoid 40.

The measuring chamber 34 has a vertical through-hole 74 having a large diameter, so that the ring 68 is movable so far in the lateral direction that the powder stream discharged from the lower end of the hose 32 laterally by-passes the measuring light barrier formed by the light source 36 and the light detector 38.

A head-piece 76 of the atomization chamber 42 has a powder-collecting hopper at the upper end. The latter consists of two hopper sections each extending over an angle of 180°, namely a first hopper section 78, whereof the wall is aligned at an angle of 45° with respect to the axis of the apparatus, as well as a second hopper section 80 extending more steeply, aligned at an angle of 25° with respect to the axis of the apparatus.

At the lower end, the two hopper sections 78, 80 lead to a common delivery cross-section, for which purpose the hopper section 78 is connected to an axial channel portion 84 by way of a rounded transition section 82.

Inserted in the head-piece 76 from the lower end face is a hopper 86 widening out conically in the downwards direction. The latter leads to a cylindrical through-hole 88, which is provided in a central housing part 90 of the atomization chamber 42. A hopper 92 again tapering conically adjoins the through-hole 88, which hopper 92 is constructed in the upper end of a base part 94 of the atomization chamber 42.

Located in the chamber defined by the housing parts 76, 90 and 94, with an identical radial spacing on all sides from the through-hole 88 and the hoppers 86, 92 is a nozzle member designated generally by the reference numeral 96, which comprises a central delivery channel for compressed air, which is open on the under side. The latter is connected by way of channels 102 provided in a radial support arm 100, to a compressed air connection opening 104, to which the solenoid valve 44 is connected.

A venturi tube 108 is inserted in a cylindrical housing bore 106 of the base part 94, adjoining the hopper 92. It may be fixed in different axial positions by a set screw 110.

Adjoining the downstream end of the venturi tube 108 is the distributor housing 48, in which, starting from the common cross-section of the venturi tube 108, various distributor channels 112 are formed, which lead to the various working lines 50.

Roughly speaking, the dusting apparatus described so far operates so that the dosing plate 20 delivers a powder stream to the hopper 28, which stream can be adjusted by its oscillation amplitude and its oscillation frequency. This powder stream is guided by way cf the hose 32 normally to a point located above the measuring light barrier formed by the light source 36 and the light detector 38 and is released there, so that the powder stream passes in free fall through the measuring light barrier. The output signal of the light detector 38 now gives a measurement of the density of the powder stream, thus of the quantity of powder atomized per unit time. The measured powder stream now passes into the atomization chamber 42 and is mixed thoroughly and uniformly therein by the compressed air stream supplied by way of the solenoid valve 44, due to which a very thin, homogeneous mist is produced.

Since the operating behaviour of the measuring light barrier formed by the light source 36 and light detector 38 changes in the course of time due to the deposition of powder and aging, the hose 32 is deflected laterally at intervals of approximately 10 seconds by the solenoid 40 to such an extent that the powder stream completely bypasses the measuring light barrier. The output signal of the measuring light barrier thus obtained is a measurement of the contamination and aging of the measuring light barrier and for further interference effects and can thus be used for compensating for corresponding measurement errors, as will be described in more detail hereafter.

FIGS. 3 and 4 show a modified measuring chamber 34. Provided in its housing is an inlet channel 14 for the powder stream and an outlet channel 118 for the powder stream enlarged in the form of a hopper at 116. These two aligning channels intersect a transverse, offset housing bore 120, in which a light barrier support 122, constructed in a similar manner to a thread roller, with two flange parts 124, 126 and a hollow hub part 128 connecting the latter, is mounted to rotate. The flange parts 124, 126 have bores 130, 132 for receiving the light source 36 or the light detector 38.

Connecting cables 134, 136 for the light source 36 and the light detector 38 are guided through the hollow hub part 128 and an adjoining hollow shaft 138. The latter is moved to and fro by a motor (not shown in detail) by an average amount of 45°, so that the light source 36 and the light detector 38 can be moved from a position fully intersecting the path of the powder stream (shown in the drawing) into a reference position located laterally outside the path of the powder stream. In this latter position, the output signal of the light detector 38 is once more used for the compensation of measuring errors caused by impurities or ageing.

In the upper part, FIG. 5 shows the control of the solenoid 40 by a free running pulse generator 140 and a power amplifier 142. The pulse generator 140 produces narrow pulses with a frequency of approximately 0.1 Hz, so that the solenoid 40 is energized briefly every 10 seconds and moves the hose 32 and thus the powder stream shown in cross-section in FIG. 5 at 144, out of the measuring light barrier defined by the light source 36 and the light detector 38.

The control terminal of a signal memory 146 also receives the output signal of the pulse generator 140, which memory is connected to the output of the light detector 38. Thus, the output signal of the light detector 38 is read into the signal memory 146 at those instants when the powder stream 144 travels past the measuring light barrier.

By way of a reversing amplifier 148, the signal stored in the signal memory 146 serves for actuating the amplification control terminal of an amplifier 150 with a controllable amplification factor. The input of the amplifier 150 receives the output signal of the light detector 38.

A powder stream signal corrected as regards disturbance effects is thus obtained at the output of the amplifier 150. The latter may also be produced alternatively according to the variation shown in broken line in FIG. 5:

A division circuit 152 receives the output signal from the pulse generator 140 at ar activating terminal, by way of an inverter 154, and thus always operates when the powder stream 144 passes through the measuring light barrier. The division circuit 152 divides the measurement signal present at the output of the light detector 38 by the reference signal made available at the output of the signal memory 146, so that one acquires at its output a powder stream signal cleaned-up as a whole with regard to impurities, aging phenomena and other interference effects.

The latter is applied to one input of a differential amplifier 156, which at its second input receives a reference signal associated with the reference density value of the powder stream and thus ultimately also the reference density of the mist produced, which reference signal, in the embodiment in question, is made available by an adjustable resistor 158.

The output signal of the differential amplifier 156 is applied to the amplification control terminal of an amplifier 160 with a controllable amplification factor. Its input is connected to the output of a sine oscillator 162, which normally operates at a frequency of approximately 50 Hz.

The output signal of the amplifier 160 is applied to a coil 164, which together with an armature 166 connected to the rod 24 as well as a helical compression spring 168 biasing the latter, forms the oscillating drive 26. The mounting of the armature 166 in the radial direction may be taken care of for example by an end plate 170 produced from sliding bearing material, of a housing 172 of the oscillating drive 26. It will be seen that the control circuit illustrated in FIG. 5 operates as a whole so that with an increasing optical density of the powder stream 144, it reduces the amplitude of the oscillating drive 26, with a decreasing density of the powder stream 144, it increases the amplitude of the oscillating drive 26. In this way, the density of the powder stream 144 is kept at the desired reference value determined by adjusting the resistor 158.

Figure 5:
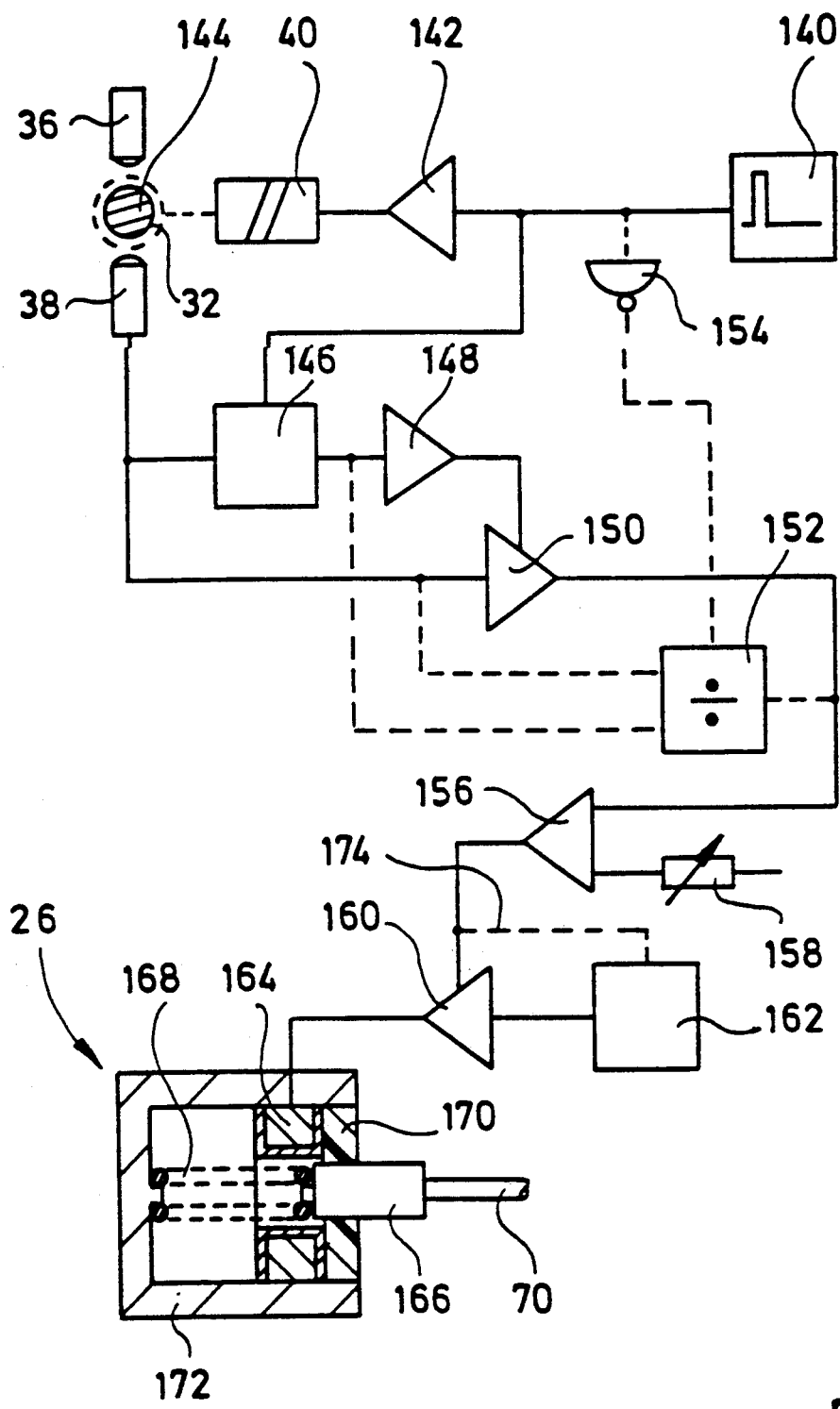
FIG. 5 is a block circuit diagram of a quantity control of the dusting apparatus according to FIG. 1.

Since the operation of the dosing plate 20 also depends on the operating frequency of the oscillating drive 26 (inertia effects in the powder volume lying on the dosing plate 20), one can replace the amplitude regulation, which was just described, completely or partly by a regulation on the basis of frequency, as indicated in FIG. 5 by the broken line 174.

It will be seen that in the manner described above, one can adjust very accurately the density of the mist produced, by using a simple light detector, which does not fulfil any high precision requirements, and a simple light source. Since the conveying path of the powder extends vertically throughout the entire dusting apparatus and the entire conveying path is free from shoulders and edges, there is no danger of the formation of deposits.

I claim:

1. Dusting apparatus which includes in combination
  (a) a container (10) for storing atomizable ground powder that has a first outlet (16),
  (b) a controllable dosing device (18-28) positioned adjacent said outlet (16) to receive powder from said outlet (16) and which delivers a free falling powder stream (144) of predetermined volume to a second outlet (30),
  (c) a powder requirement sensor (36, 38) which is mounted to monitor the powder flow from said second outlet (30) and which regulates said dosing device (18-26),
  (d) an atomization device (42) connected to said second outlet (30) of the dosing chamber (18-28) which forms the fine particles of the powder stream into a mist which exits through a third outlet (48),
  (e) at least one nozzle connected to said third outlet (48) for discharging the mist-like powder stream formed by said atomization device (42) toward an object (56) to be dusted,
  (f) said sensor (34) including
    (1) a measuring means (36, 38) having a measuring axis through which the powder stream (144) is guided in free fall and which means measures the stream density, and
    (2) positioning means (32, 40; 122) for selectively establishing one of two relative positions between the free falling powder stream (144) and the measuring means (36, 38) the powder stream (144) intersecting the measuring means (36, 38) in the first of said two relative positions while passing clear of the measuring means (36, 38) in the second of said two relative positions.

2. Dusting apparatus according to claim 1 wherein the positioning means for selectively establishing one of two relative positions between the free-falling powder stream (144) and the measuring means (36, 38) comprise a flexible piece of hose (32) having a discharge end that lies above the measuring means (36, 38) and which can be moved in a direction perpendicular to the measuring axis of the measuring means (36, 38).

3. Dusting apparatus according to claim 2 wherein the discharge end of the piece of hose (32) is guided radially in a ring (68), which is positively connected to an output part of a solenoid (40).

4. Dusting apparatus according to claim 2 wherein a collecting hopper (28, 80) is provided below a region swept by the powder stream (144) upon movement of the flexible piece of hose (32).

5. Dusting apparatus according to claim 4 wherein in the peripheral direction, the collecting hopper comprises two successive wall sections (78, 80) of different inclination with respect to a hopper axis, the more steeply inclined wall section (80) lying below the path of the flexible piece of hose (32).

6. Dusting apparatus according to claim 5 wherein more steeply inclined wall section (80) of the collecting hopper is inclined at an angle of approximately 45° and the less steeply inclined wall section (80) of the collecting hopper is inclined at an angle of approximately 25° to the axis of the collecting hopper.

7. Dusting apparatus according to claim 1 wherein the positioning means includes means (122, 138) for shifting the measuring means (36, 38) in a direction perpendicular to the direction of the powder stream (144).

8. Dusting apparatus according to claim 4 wherein adjoining a lower end of the collecting hopper (78, 80; 116) receiving the free-falling powder stream (144) behind the measuring means (36, 38) is an atomization chamber (86, 88, 92) of the atomization device (42), which comprises a first chamber section (86) widening out conically, a second chamber section (88) having a constant cross-section as well as a third chamber section (92) tapering conically, and that located at a substantially constant radial distance from walls of the atomization chamber, in its interior, is a nozzle member (96), whereof a lower conical end section comprises a central, axial discharge opening (98) for the gaseous carrier stream.

9. Dusting apparatus according to claim 8 wherein a venturi insert (108) is disposed below the atomization chamber.

10. Dusting apparatus according to claim 9 wherein the venturi insert (108) is fixed in an axially adjustable manner to a housing of the atomization device (42).

11. Dusting apparatus according to claim 10 which includes a distributor device (48) located below the venturi insert (108), in which a plurality of discharge channels (112) are formed, which originate jointly at a downstream end of the venturi insert (108) and then diverge.

12. Dusting apparatus according to claim 1 wherein the dosing device comprises a dosing plate (20) located at a predetermined axial distance below the outlet of the storage container, is able to reciprocate perpendicularly to the axis of the outlet at adjustable momentum by virtue of a momentum control circuit (156 to 160) which varies the momentum of the reciprocating movement of the dosing plate (20) inversely to the change of output signal of the measuring means (36, 38).

13. Dusting apparatus according to claim 1 which includes a controllable measuring amplifier (150) following the measuring means (36, 38) and by a signal memory (146), also following the measuring means (36, 38), which is activated when said second relative position between the measuring means (36, 38) and the free-falling powder stream (144) is established, and whereof an inverted output signal is supplied to a control terminal of the measuring amplifier (150).

14. Dusting apparatus according to claim 1 which includes a division circuit (152) following the measuring means (36, 38) and by a signal memory (146) also following the measuring means (36, 38) which is activated when said second relative position between the measuring means (36, 38) and the free-falling powder stream (144) is established, inputs of the division circuit (152) being connected to the outputs of the measuring means (36, 38) and of the signal memory (146).

15. Dusting apparatus according to claim 1 wherein the measuring means (36, 38) comprises a light barrier operating in transmission.

16. Dusting apparatus according to claim 1 wherein the positioning means includes means (122, 138) for shifting the measuring means (36, 38) in a direction perpendicular to the direction of the powder stream (144).

17. Dusting apparatus according to claim 16, wherein a transmitter (36) and a receiver (38) of the measuring means are disposed in flange parts (124, 126) rigidly connected by a hub part (128), which parts are mounted to rotate in a measuring chamber housing (34).

18. Dusting apparatus according to claim 16 wherein a collecting hopper (116) receives the free-falling powder stream (144) behind the measuring means (36, 38).

* * * * *

UNITED STATES PATENT AND TRADEMARK OFFICE
CERTIFICATE OF CORRECTION

PATENT NO. : 5,090,626
DATED : February 25, 1996
INVENTOR(S) : Platsch

It is certified that error appears in the above-identified patent and that said Letters Patent is hereby corrected as shown below:

On the title page, item

"[73]   Assignee:    Industrieelektronik Dr.-Ing. Walter Klaschka GmbH & Co., Fed. Rep. of Germany", and should read -- [73]   Assignee:    Industrieelektronik Dr.-Ing. Walter Klaschka GmbH & Co., Fed. Rep. of Germany (Part Interest)--.

Signed and Sealed this

Sixth Day of July, 1999

Attest:

Q. TODD DICKINSON

*Attesting Officer*     *Acting Commissioner of Patents and Trademarks*